United States Patent [19]
Matuszewski et al.

[11] Patent Number: 4,758,520
[45] Date of Patent: Jul. 19, 1988

[54] CHEMILUMINESCENCE METHOD FOR ASSAYING COMPOUNDS CONTAINING PRIMARY AMINO GROUPS USING 1-CYANO-2-SUBSTITUTED BENZ(F)- OR NAPHTH(F)-ISOINDOLE FLUORESCERS

[75] Inventors: Bodgan Matuszewski, Lansdale, Pa.; Richard S. Givens, Lawrence, Kans.; Robert G. Carlson, Lawrence, Kans.; Takeru Higuchi, Lawrence, Kans.; Takao Kawasaki, Lawrence, Kans.; Osborne S. Wong, Lenexa, Kans.

[73] Assignee: Oread Laboratories, Inc., Lawrence, Kans.

[21] Appl. No.: 837,671

[22] Filed: Mar. 10, 1986

[51] Int. Cl.⁴ .................... G01N 21/76; G01N 33/52; G01N 33/68
[52] U.S. Cl. .......................... 436/86; 436/89; 436/109; 436/93; 436/111; 436/128; 436/131; 436/135; 436/172
[58] Field of Search ............. 436/86, 89, 90, 109, 436/111, 128, 131, 135, 161, 172, 93

[56] References Cited

U.S. PATENT DOCUMENTS

| | | |
|---|---|---|
| 3,511,612 | 5/1970 | Kennerly et al. |
| 3,539,794 | 11/1970 | Rauhut et al. |
| 3,557,233 | 1/1971 | Zweig et al. |
| 3,576,987 | 5/1971 | Voight et al. |
| 3,578,962 | 5/1971 | Gerber |
| 3,597,362 | 8/1971 | Bollyky et al. ............ 436/135 X |
| 3,689,391 | 9/1972 | Ullman |
| 3,691,085 | 9/1972 | Roberts et al. |
| 3,704,231 | 11/1972 | Bollyky |
| 3,704,309 | 11/1972 | Maulding |
| 3,718,432 | 2/1973 | Roth .......................... 436/90 X |
| 3,718,599 | 2/1973 | Rauhut |
| 3,729,426 | 4/1973 | Zweig et al. |
| 3,775,336 | 11/1973 | Kasulin et al. |
| 3,892,530 | 7/1975 | Felix et al. ................. 436/90 |
| 3,933,430 | 1/1976 | Hare ......................... 436/90 |
| 4,359,323 | 11/1982 | LePage ...................... 436/89 |
| 4,647,532 | 3/1987 | Watanabe et al. ........ 436/135 X |

OTHER PUBLICATIONS

Honda et al., J. of Chromatography, vol. 303, pp. 173–176, 1984.
Kobayashi et al., Anal. Biochem., vol, 112, pp. 99–104, 1981.
Honda et al., J. of Chromatography, vol. 316, pp. 501–505, 1984.
Rauhut et al., J. Am. Chem. Soc., vol. 89, pp. 6515–6522, 1967.
Kobayashi et al., Anal. Chem., vol. 52, pp. 424–427, 1980.
Miura et al., Anal. Biochem., vol. 137, pp. 432–437, 1984.
Ishida et al., J. of Chromatography, vol. 204, pp. 143–148, 1981.
Gardner et al., Anal. Biochem, vol. 101, pp. 61–65, 1980.
Allison et al., Anal. Chem., vol. 56, pp. 1089–1096, 1984.

Primary Examiner—Barry S. Richman
Assistant Examiner—Robert J. Hill, Jr.
Attorney, Agent, or Firm—Burns, Doane, Swecker & Mathis

[57] ABSTRACT

A chemiluminescence method for assaying compounds containing primary amino groups using 1-cyano-2-substituted benz(f)- or naphth(f)-isoindole fluorescers is disclosed. The 1-cyano-2-substituted benz(f)- or naphth(f)-isoindole (CBI or CNI) is formed by reacting a compound containing a primary amino group with naphthalene-2-3-dicarboxaldehyde or anthracene-2,3-dicarboxaldehyde in the presence of cyanide ion. The reaction product of hydrogen peroxide with an oxalate ester is then combined with the CBI or CNI to form an analyte which exhibits chemiluminescence. A detector is used to measure the chemiluminescence emission from the chemiluminescence derivatized analytes. Compounds containing primary amino groups which may be assayed according to the present invention include primary amines, amino acids, peptides and catecholamines. The method can also be adapted to the analysis of trace amounts of cyanide ion and hydrogen peroxide.

17 Claims, 5 Drawing Sheets

CHEMILUMINESCENCE METHOD FOR ASSAYING COMPOUNDS CONTAINING PRIMARY AMINO GROUPS USING 1-CYANO-2-SUBSTITUTED BENZ(F)- OR NAPHTH(F)-ISOINDOLE FLUORESCERS

BACKGROUND OF THE INVENTION i. Field of the Invention

The present invention relates generally to methods for assaying compounds containing primary amino groups and more particularly to a chemiluminescence method wherein a fluorescer analyte containing the primary amino group is chemically excited to yield a readily detectable and quantifiable species.

ii. Description of the Prior Art

Fluorescence detection techniques find wide application in the field of analytical chemistry. Such techniques typically involve the exposure of a sample containing one or more moieties of interest to light of a given wavelength whereby a characteristic emission is observed with respect to each of the moieties. It is then possible to obtain both a qualitative and quantitative assay of the sample.

The problem with such absorption detection techniques, however, is that they often give rise to a high background signal which reduces their sensitivity. More specifically, in fluorescence detection techniques, characterized by light induced emission from the singlet excited state, stray light as well as other scattering phenomena namely, Raleigh and Raman scattering, result in an increase in the background signal thereby reducing the sensitivity of fluorescence detection techniques. Interference from both stray light and Rayleigh scattering can be eliminated by employing properly designed cell compartments and by using emission filters and monochromators. Although interference from Raman scattering can also be eliminated, such requires even more sophisticated techniques. Accordingly, although it is possible to substantially eliminate the background interference in fluorescence analytical techniques, such is achieved only by virtue of a great deal of additional time and expenditure.

Because of the difficulties encountered in the art with respect to high sensitivity fluorescence detection techniques, techniques employing chemiluminescence have been sought. Unlike fluorescence techniques wherein a compound of interest is raised to the singlet excited state by the absorption of ultraviolet or visible radiation, chemiluminescence techniques effect excitation of the compound of interest by a chemical reaction. They therefore do not give rise to the same light scattering phenomena observed with respect to absorption techniques.

To perform chemiluminescence techniques, a chemical reaction is carried out which transfers energy to a fluorescer (or energy acceptor) thus raising the fluorescer to an excited state. The excited fluorescer itself then returns to the ground state by releasing a photon or by other non-emissive processes. The photon release, of course, is registered by a suitable detection device.

Despite the indisputable advantages of chemiluminescence techniques over fluorescence techniques, the practice of chemiluminescence techniques has not been widespread. The reason for this relates to the extreme difficulty with which compounds can be made to exhibit chemiluminescence. More specifically, the number of compounds which exhibit fluorescence, i.e., which emit a photon upon excitation by light, is quite limited to begin with. Of this limited number of fluorescence compounds, only a still smaller number of compounds will exhibit chemiluminescence, i.e., emit a photon upon excitation by a chemical reaction. Add to this the fact that application of chemiluminescence to assaying techniques requires that the compound exhibiting chemiluminescence be derivable from the materials of interest (primary amino compounds in the case of the present invention) and it is not surprising that there are few effective assaying methods of employing chemiluminescence techniques which are available.

In one chemiluminescence technique, a mixture of an aryl oxalate with hydrogen peroxide is used to activate a fluorescer formed from dansylated amino acids, i.e., amino acids reacted with 5-dimethylaminonaphthalene-sulfonyl chloride followed by acid hydrolysis. The individual dansylated amino acids themselves are initially fractionated by high performance liquid chromatography. The detection limits for such activated amino acid fluorescers is 2 to 5 femtomoles when detection is carried out with a specifically designed detector employing a spiral flow cell interfaced to a single photon counting photomultiplier. Fluorescers formed by dansylating amino acids and primary amines were shown to give the lowest detection limits, i.e., 0.8 to 14 femtomole for various aliphatic primary amines. Fluorescers formed by reacting aliphatic amines with 4-chloro-7-nitrobenzo-1,2,5-oxadiazole (NBD-Cl) and o-phthaldehyde (OPA) gave detection limits ranging from 19 to 270 and 94 to 580 femtomoles respectively.

Although the above reported detection limits obtainable by employing dansylated derivatives as fluorescers in chemiluminescence assaying techniques are quite good, their applicability to samples which are fractionated by high performance liquid chromatography techniques is somewhat limited. Reverse phase high performance liquid chromatography techniques, i.e., wherein the mobile phase is organic-water mixture typically require the presence of substantially and highly variable concentrations of water. The fluorescence yields $\phi f$ of dansylated amino acids, however, are highly affected by such variations in solvent. Thus, dansylated amino acids which have $\phi f$ values of 0.3 to 0.7 in organic solvents were found to have $\phi f$ values of 0.053 to 0.091 in water. Accordingly, the fluorescence yield $\phi$ of dansylated amino acids fractionated by high performance liquid chromatography is often at an unacceptably low level for detecting and quantifying very low amounts of those amino acids.

SUMMARY AND OBJECTS OF THE INVENTION

In view of the foregoing limitations and shortcomings of prior art chemiluminescence techniques as well as other disadvantages not specifically mentioned above, it should be apparent that there still exists a need in the art for a chemiluminescence method for assaying very minute quantities (femtomoles) of analytes containing primary amino groups which is not adversely affected by the conditions typically encountered in HPLC separations or other separation techniques. It is, therefore, a primary objective of the present invention to fulfill that need by providing new fluorescer compounds which are formed from compounds containing primary amino groups and which can be activated to exhibit strong chemiluminescence even in varying solvent environments.

It is another object of the invention to provide a method for assaying compounds containing a primary amino group which enables detection of femtomole quantities or less of such compounds.

Still another object of this invention is to provide a method for assaying compounds containing a primary amino group by chemiluminescence which provides greater sensitivity.

A further object of this invention is to provide a method for assaying compounds containing a primary amino group by chemiluminescence employing a new class of oxalate esters which enhance chemiluminescence efficiency.

Another object of this invention is to provide a method for assaying cyanide and hydrogen peroxide using the naphthalene-2,3-dicarboxaldehyde-primary amine (NDA-primary amine) or anthracene-2,3-dicarboxaldehydeprimary amine (ADA- primary amine) fluorescers in the chemiluminescence method.

Briefly described, those and other objects of the invention are accomplished by providing a method for assaying compounds containing a primary amino group comprising:

(i) reacting a compound containing a primary amino group with naphthalene-2,3-dicarboxaldehyde (NDA) or anthracene-2,3-dicarboxaldehyde (ADA) in the presence of cyanide ion to form a 1-cyano-2-substituted-benz(f)isoindole or a 1-cyano-2-substituted-naphth(f)isoindole as follows:

(ii) mixing an oxalate ester and hydrogen peroxide with the 1-cyano-2-substituted benz(f)isoindole fluorescer or the 1-oyano-2-substituted naphth(f)isoindole fluorescer to form chemiluminescence analytes; and (iii) detecting and measuring the chemiluminescence emission from said chemiluminescent analytes by means of a detector.

Preferably, after the mixture of compounds containing primary amino groups is reacted with NDA or ADA to form the adduct, it is fractionated by high performance liquid chromatography and the various adduct fractions combined with the oxalate ester and hydrogen peroxide for subsequent chemiluminescence analysis. Alternatively, the mixture may be fractionated prior to reaction with NDA or ADA.

With the foregoing and other objects, advantages, and features of the invention that will become hereinafter apparent, the nature of the invention will be more clearly understood by reference to the following detailed description of the invention, the appended claims and the drawings.

BRIEF DESCRIPTION OF THE DRAWINGS

FIGS. 4 A-B is a graph comparing the Chemiluminescence versus Fluorescence Detection of CBI-ALA in a flow High Performance Liquid Chromatography System;

DETAILED DESCRIPTION OF PREFERRED EMBODIMENTS

Figure 1:
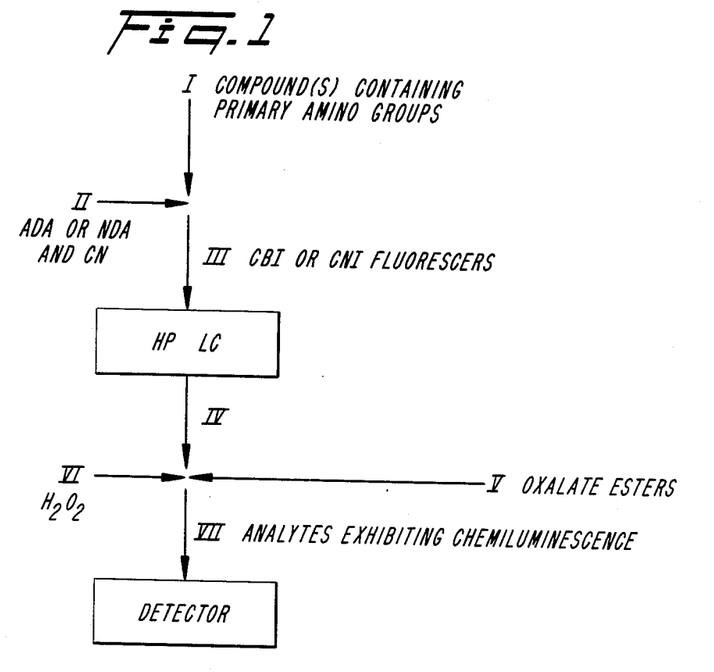
FIG. 1 is a flow diagram of one embodiment of the overall process of the invention.

The overall method of a preferred embodiment the present invention is illustrated as a flow diagram at FIG. 1. A sample containing primary amino compounds (stream I) is first reacted with either naphthalene-2,3-dicarboxaldehyde (NDA) or anthracene-2,3-dicarboxaldehyde (ADA) (stream II) in the presence of cyanide ion to form the derivative fluorescers CBI and CNI respectively (stream III). The sample containing the CBI or CNI derivatives is then fractionated by a technique such as high performance liquid chromatography to yield an effluent (stream IV) containing fractionated CBI or CNI derivatives of the primary amino compounds. The oxalate ester, in ethyl acetate solvent, (stream V) and the $H_2O_2$, in tetrahydrofuran or appropriate solvent (stream VI) are combined with the stream IV of the CBI or CNI fluorescers to effect chemiluminescence (stream VII) which is then sent on to a detection device for analysis.

(i) Materials which may be assayed by the method of the present invention

The present invention provides an effective method for assaying a single compound or a mixture of compounds containing primary amino groups. Included among compounds containing primary amino groups are amino acids, primary amines, peptides and catecholamines.

Any sample which is believed to contain one or more compounds containing primary amino groups may be assayed according to the present invention. Thus, effective assays may be obtained from both aqueous and organic solvents. Additionally, samples containing amounts as low as 1 nanomolar of primary amino compound and as high as 1 millimolar of primary amino compound may be assayed. While higher concentrations of primary amino compounds could also be assayed, much less sophisticated techniques are generally suitable at such higher concentration levels.

Typically, the materials which are assayed originate from biological fluids such as urine, whole blood, plasma, serum and pharmaceutical dosage forms.

(ii) Formation of adducts from primary amino compounds and NDA or ADA

The sample containing a single primary amino compound or a mixture of primary amino compounds is reacted with NDA in the presence of cyanide to form a 1-cyano-2-substituted-benz(f)-isoindole (CBI) or, alternatively, with ADA in the presence of cyanide to form a 1-cyano-2-substituted-naphth(f)isoindole (CNI) as follows:

naphthalene-2,3-dicarboxaldehyde 1-cyano-2-substituted-benz(f)isoindole anthracene-2,3-dicarboxaldehyde 1-cyano-2-substituted-naphth(f)isoindole Of the two reactions depicted above for forming isoindoles from primary amines and dialdehydes, that employing NDA is clearly preferred.

NDA as well as ADA are both compounds which are known in the art. Their preparation is therefore not further described herein.

The formation of CBI from compounds containing primary amino groups is described in detail in U.S. patent application Ser. No. 707,676 filed Mar. 4, 1985, the disclosure of which is hereby incorporated by reference. Generally, CBI is formed by reacting the compounds containing primary amino groups with NDA and cyanide ion under mildly alkaline conditions, i.e., at pH levels of between about 9 and 10. It should be noted that CBI fluoresces when exposed to light having a wavelength of 420 nm. Because of the disadvantages inherent to fluorescence techniques, the present invention provides a method through which CBI as well as CNI can be made to chemiluminesce.

(iii) Fractionation of the samples containing a mixture of compounds having primary amino groups If the starting reagent includes two or more compounds containing primary amino groups, it is generally subjected to a fractionation step. It is possible to carry out the fractionation before or after formation of the CBI or CNI adducts of the primary amines. The most preferred fractionation technique is high performance liquid chromatography (HPLC) which is a well known fractionation technique. Of course, if only one compound containing a primary amino group is present in the sample to be assayed, fractionation may not be necessary.

High performance liquid chromatography of the samples according to the present invention was carried out with a Waters 590 programmable solvent delivery system, a Rheodyne 7125 injector equipped with a 20 microliter loop and a Supelcosil LC18 column having dimensions of 25 cm×4.6 mm or 15 cm×4.6 mm. Generally, a 70:30 (w/w) mixture of HPLC grade acetonitrile/imidazole buffer (0.0025M in $H_2O$, pH=7.2) was employed as the mobile phase with a flow rate of 1 mL/min. Of course, other HPLC systems as well as other fractionation techniques may be effectively employed according to the present invention.

(iv) Chemiluminescence activation of the CBI or CNI fluorescers

After the CBI or CNI adducts are formed and, if desired, fractionated, they are activated by the addition of an oxalate ester and hydrogen peroxide which brings fluorescers such as CBI or CNI from the ground state to the exited state. Oxalate esters which may be used according to the present invention include the new oxalates bis-(2,4-difluorophenyl)oxalate (2,4-DFPO) and bis-(2,6-difluorophenyl)oxalate (2,6-DFPO) as well as the previously known oxalates bis-(2,4-dinitrophenyl)oxalate (2,4-DNPO); bis-(2,4,6-trichlorophenyl)oxalate (TCPO); and bis-(pentafluorophenyl)oxalate (PFPO).

The synthesis of the oxalate esters 2,4-DNPO, TCPO and PFPO is known in the art. For example, a method for producing DNPO is described by M. M. Rauhut; L. J. Bollyky; B. G. Roberts; M. Loy; R. H. Whitman; A. V. Iannotta; A. M. Semsel; and R. A. Clarke in "Chemiluminescence from Reactions of Electronegatively Substituted Aryl Oxalates with Hydrogen Peroxide and fluorescence Compounds", *Journal of the American Chemical Society*, 89:25, Dec. 6, 1967 at pages 6515–6522. DNPO was prepared by first drying a solution of 368.2 g (2 moles) of 2,4-dinitrophenol in 5L of reagent grade benzene by azeotropic distillation of 1L of solvent. The dried solution was cooled to 10° C. under nitrogen, and 202.4 g (2 moles) of freshly distilled triethylamine was added. Oxalyl chloride (139.6 g; 1.1 moles) was then added with stirring during 30 min using an ice bath to maintain the reaction temperature between 10 and 25°° C.

The resulting yellow slurry was stirred 3 hr. and evaporated to dryness under reduced pressure. The solid was stirred well with 1L of chloroform to dissolve triethylamine hydrochloride, and the product was collected on a sintered-glass funnel, washed with chloroform, and dried under vacuum. Recrystallization from nitrobenzene below 100° C. provided 151.3 g (35.8%) of pale yellow crystals having a melting point between 189°–192° C.

Preparation of PFPO is also described. The other known oxalate ester TCPO can be prepared generally by the above-described process with minor modifications, which would be readily appreciated by persons skilled in the art.

The procedure for synthesizing the new compounds 2,4- and 2,6-DFPO proceeds as follows. First, triethylamine ($Et_3N$) is distilled and combined with either a 2,4- or a 2,6-fluorophenyl compound in a dry benzene solution at 0° C. Oxalyl chloride is then added dropwise to the stirred solution under a nitrogen atmosphere and the reaction allowed to proceed overnight at room temperature. Generally, about 2 parts by weight of $(Et)_3N$, 5 parts by weight phenyl compound, and 1.3 parts by weight oxalyl chloride in an excess volume of dry benzene may be employed. Of course, persons skilled in the art will appreciate that these are merely to be used as a guide and do not necessarily represent the optimal system achievable.

In the case of 2,4-DFPO, the solid mixture of oxalate ester and triethylammonium hydrochloride (ET$_3$N HCl) obtained after synthesis was treated with warm benzene to dissolve the oxalate thus allowing separation of undissolved Et$_3$N HCl from the oxalate as well as from the benzene portion. After solvent removal and recrystallization from the same solvent, crystalline needles of 2,4-DFPO were obtained in 58% yield.

In the case of 2,6-DFPO, an attempt was made to remove the Et$_3$N HCl from the oxalate ester by dissolving the former in petroleum ether. However, this appeared very inefficient. Therefore, oxalate ester was dissolved in warm benzene and worked up as described above for 2,4-DFPO to yield a major portion of the desired 2,6-DFPO. The remaining solid material (mostly Et$_3$N HCl) was combined with the petroleum ether washings, and the mixture was washed with water. The organic layer was dried over MgSO$_4$ and after solvent removal, additional portions of 2,6-DFPO were obtained. The combined 2,6-DFPO fractions were recrystallized from ethyl acetate-petroleum ether to give colorless crystals of 2,6-DFPO in 78% yield.

The new oxalate ester 2,6-DFPO was found to be superior to TCPO for detection of CBI derivatives under the conditions examined, giving higher total chemiluminescence intensities when measured in static system, and lower detection limits in a HPLC-chemiluminescence flow system. Currently TCPO has been used almost exclusively in reported HPLC-chemiluminescence studies. Another advantage of using 2,6-DFPO over TCPO is a seven-fold higher solubility of this ester in ethyl acetate, which allows one to increase the concentration of chemiluminescence reagent in the system, and further increase the sensitivity of detection of CBI derivatives.

The oxalate ester/H$_2$O$_2$ reaction product is formed generally by reacting a 0.01 to 1.0M solution of hydrogen peroxide with a 0.005 to 0.05M solution of oxalate ester in a suitable solvent such as ethylacetate or THF.

When the HPLC system described above is employed, the oxalate ester/H$_2$O$_2$ reaction product was prepared as follows. First, a 5.0 mM solution of oxalate ester in an ethyl acetate solvent and a 1M solution of H$_2$O$_2$ in THF were combined in a ratio of 1:2. Ethyl acetate was selected as the solvent for the oxalate ester since TCPO is quite stable in ethyl acetate for a prolonged period of time. In order to avoid precipitation of TCPO after mixing with the HPLC effluent, the flow rate and water content in the HPLC mobile phase were kept at a minimum, as a result of which the binary solvent selection for the HPLC separation procedure is somewhat limited. Specifically, mobile phase flow rates were limited to 0.3 to 0.5 mL/min with a water content of less than 50%. H$_2$O$_2$ in THF was used exclusively in the HPLC system in combination with oxalate esters in ethyl acetate since THF diminishes the problem of TCPO precipitation.

Two syringe pumps (Nester/Faust), each with a 500 ml capacity, were used to deliver the oxalate ester/ethyl acetate and H$_2$O$_2$/THF solutions to a mixer where the two solutions were mixed by a mechanical stirrer. This chemiluminescence reagent mixture was delivered to a second interface mixture with 0.25 mm stainless steel tubing. The flow rates of the oxalate ester and peroxide reagents were maintained at 1.0 and 2.0 mL/min, respectively. The second interface mixer had a dead volume of approximately 25 microliters. The chemiluminescence reagent was then mixed with the effluent from the HPLC column and sent to the detector as described below.

After mixing an oxalate ester with H$_2$O$_2$, the resulting solution is mixed with the CBI or CNI adducts formed from primary amino groups. A chemiluminescence species is thereby generated.

Generally, the oxalate ester/peroxide mixture prepared above is mixed directly with the fractionated HPLC effluent containing CBI or CNI. The amount of oxalate ester/peroxide added should be about 10-fold or greater than that of the CBI or CNI adduct which is present at a concentration of less than 1 mM.

(v) Detection and analysis of chemiluminescence analytes

The chemiluminescence properties of the newly introduced 1-cyano-2-substituted-benz(f)isoindole derivatives were examined in both a static flow detection system and in a specifically designed HPLC/chemiluminescence flow detection system. The static system was used to determine the chemiluminescence efficiencies as a function of time for various oxalate ester and CBI and CNI derivatives.

Figure 2:
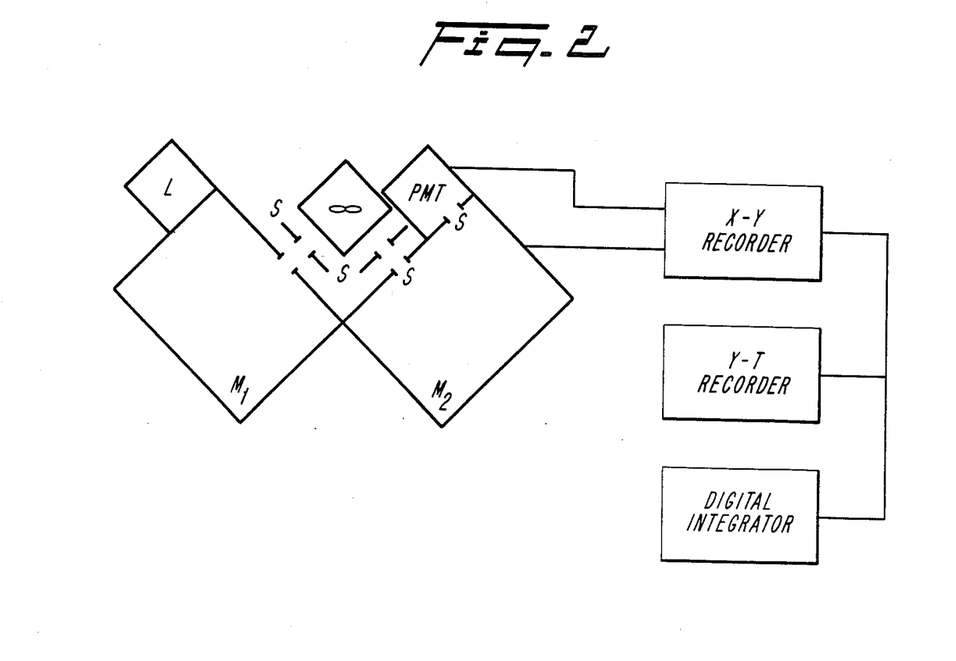
FIG. 2 is a schematic illustration of a Static System Chemiluminescence Analyzer.

The static detector system was a modified Aminco-Bowman spectrofluorometer SPF 4-8940 SP. As illustrated in FIG. 2, the system comprises a xenon lamp, excitation and emission monochromators, a photomultiplier tube, four slits $S_1$-$S_4$ (0.5 to 4.0 mm) and a chemiluminescence reaction cell having the dimensions 1.0×1.0 cm, with a 3.0 mL capacity. The cell compartment of the above-described system was modified to allow mixing of the content of the cell by electromagnetic stirring. Each oxalate ester/ethyl acetate solution was mixed first with a fluorescer dissolved in ethyl acetate. The emission monochromator was set at the emission maximum of a given analyte. A solution of H$_2$O$_2$/THF was next added to the cell, the shutter of the photomultiplier tube opened, and a plot of the chemiluminescence intensity as a function of time recorded using a strip chart recorder. The integrated area under the trace was taken as a relative measure of the total chemiluminescence efficiency generated in a given system. The oxalate ester, hydrogen peroxide and fluorescer concentration were held constant for each run allowing a direct comparison of the relative chemiluminescence yields from a series of oxalate esters with a given energy acceptor.

The static system setup illustrated in FIG. 2 allows measurement of the fluorescence emission spectra of a fluorescer before and after chemiluminescence reaction thus permitting study and comparison of various energy acceptors under chemiluminescence reaction conditions. In these studies, the excitation lamp was turned on and the fluorescence spectrum recorded with an X-Y recorder (fluorescence intensity vs. emission wavelength).

Figure 3:
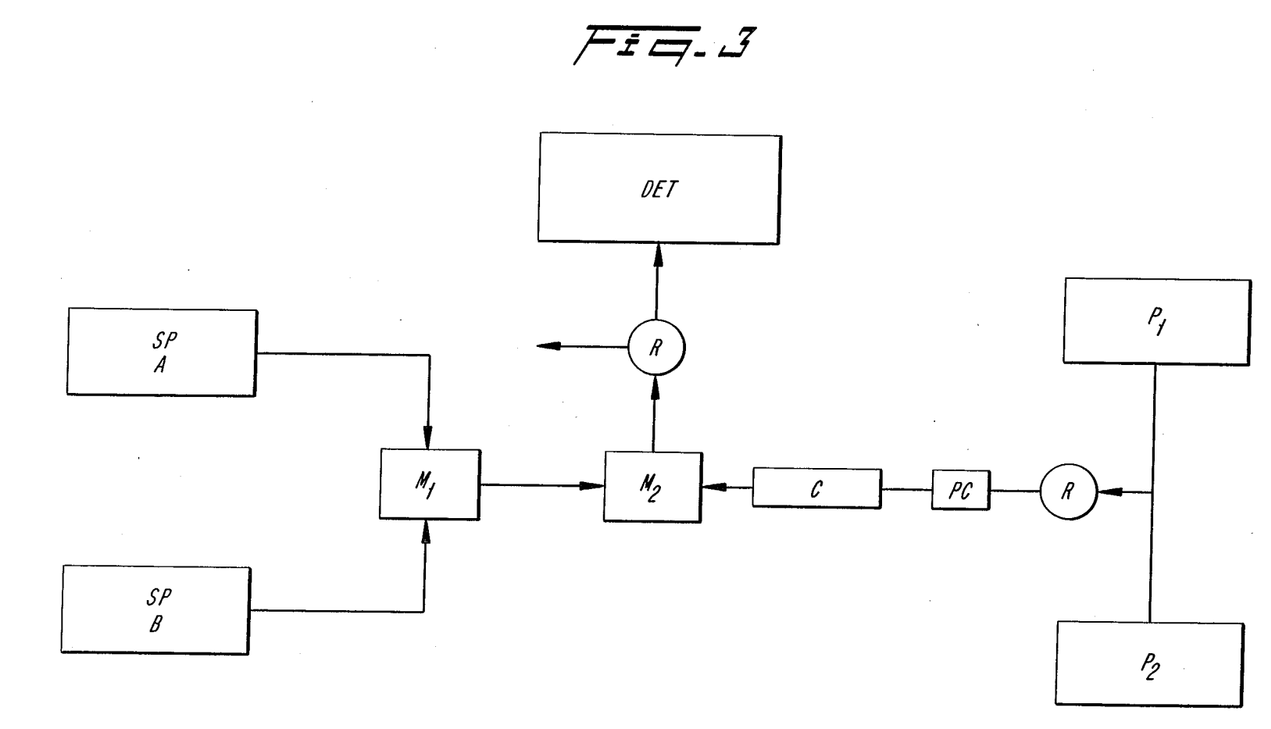
FIG. 3 is a schematic illustration of a High Performance Liquid Chromatography Post Column Flow Detection System.

The specially designed HPLC/chemiluminescence flow detection system is illustrated at FIG. 3. The system comprises a Kratos/Schoeffel FS 970 fluorescence detector with a 5 microliter flow cell. A cutoff emission filter with an emission wavelength of 418 nm was employed. The detector was equipped with a 5 microliter flow cell. The photomultiplier tube voltage and full scale outputs are adjustable to various experimental modes.

As further illustrated in FIG. 3, the fluorescence detector DET is connected to a Rheodyne injector R, type 7125 which in turn is connected to a mixer $M_2$ wherein effluent from the HPLC column and the oxalate ester/peroxide reaction product are combined. The system is adapted for stop-flow measurements as well as for diverting the flow of reagents with the above-described Rheodyne 7125 valve placed between the mixer $M_2$ and the detector DET. The sample can thus be retained in the detector cell allowing monitoring of the decay of the chemiluminescence signal as a function of time.

(vi) Assay of trace levels of hydrogen peroxide or cyanide ion using CBI or CNI adducts The chemiluminescence method of the present invention using CBI and CNI adducts is also appreciable to the assay of trace quantities of both cyanide and hydrogen peroxide. To assay trace quantities of hydrogen peroxide, an oxalate ester and a known quantity of premade CBI or CNI adduct are added to the sample containing the peroxide. Because chemiluminescence of the mixture requires the presence of peroxide and because all other variables in the above-described system are known, the intensity of the resulting chemiluminescence can be utilized to ascertain the amount of $H_2O_2$ present in the system.

In similar fashion, trace amount of cyanide may be assayed by using controlled amounts of ADA or NDA and primary amino compounds to form a quantity of CBI or CNI which depends upon the amount of cyanide ion. The resulting adduct can then be mixed with oxalate ester and peroxide to form an analyte which exhibits a degree of chemiluminescence which is also dependent on the quantity of cyanide ion present.

The following Examples are given by way of illustration and should not be construed as limiting the scope of the subject matter disclosed and claimed.

COMPARATIVE EXAMPLE 1

Chemiluminescence Efficiency for CBI Derivatives versus Dansyl Amino Acid Derivatives Using Various Oxalate Ester Activators.

The chemiluminescence efficiency of dansylatedasparagine, Dans-ASN was compared to that of CBI-t-BuA using the high energy species formed from the oxalate esters TCPO and 2,6-DFPO.

Dans-ASN was chosen from among other dansylated amino acids because of its good solubility in organic solvents and because it gave the same or a higher intensity signal than other dansylated amino acids in an HPLC/chemiluminescence detection system. Therefore, the improvement of chemiluminescence efficiency obtained for CBI derivatives in comparison with Dans-ASN should be at least as good, if not better, than for all other dansylated amino acids. This appeared to be the case for the Dans-GLY which was also briefly studied.

To carry out the comparison, equimolar amounts of the CBI adduct according to the invention and the dansylated adduct of the prior art were assayed namely, $3.8 \times 10^{-6}M$ of fluorescent adducts in ethyl acetate. The dansylated amines were purchased and CBI adducts of the invention were prepared by reacting the amines with NDA and CN as described in Application Ser. No. 707,676, supra. The high energy species was formed by combining $1 \times 10^{-3}M$ oxalate ester (either TCPO or 2,6-DFPO) with 0.1M $H_2O_2$ in a solvent comprising an 80/20 (by volume) mixture of ethyl acetate and THF. The chemiluminescence efficiency was measured at 505 and 480 nm for Dans-ASN and CBI-t-BuA respectively using an Aminco-Bowman spectrofluorometer detector in a static system. The lengths of time for storage of oxalate ester solutions in ethyl acetate prior to actual measurements were 1 day for TCPO and 6 days for 2,6 DFPO. The results indicate that total chemiluminescence yields are not due to differences in the stability of the oxalates in ethyl acetate. Freshly prepared $3.8 \times 10^{-6}M$ stock solutions of energy acceptors (Dans-ASN and CBI-t-BuA) in ethyl acetate were used.

The results of the comparative experiment are set forth in Table I as follows:

TABLE I

| Oxalate Ester | Dans-ASN | | CBI-t-BuA | |
|---|---|---|---|---|
| | a | b | a | b |
| TCPO | 90,000 | (4:96) | 106,000 | (30:70) |
| 2,6-DFPO | 22,700 | (15:85) | 186,000 | (30:70) | a Total chemiluminescence efficiency in arbitrary units, measured as an area under the intensity vs. time plot.
b Ratio of chemiluminescence efficiency for the first 3 min and after 3 min, after initial chemiluminescence generation.

Analysis of the data in Table I clearly shows that CBI-t-BuA gave a significantly higher chemiluminescence efficiency than Dans-ASN, especially when 2,6-DFPO was used as the chemiluminescence activator. On the other hand, the total chemiluminescence efficiency (integrated area under curve) for Dans-ASN was larger with TCPO than 2,6-DFPO. In this case, about three times more light was emitted in the first three minutes for 2,6-DFPO than for TCPO. The time dependence of the chemiluminescence intensity was quite complex in all cases, revealing several maxima within the time span of reaction.

The fractions of total chemiluminescence efficiency up to 3 min of chemiluminescence reaction and after 3 min were calculated and are also given in Table I. For 2,6-DFPO/CBI-t-BuA, the percentage of total chemiluminescence efficiency in the early stages of reaction was relatively higher than for TCPO/Dans-ASN. This feature might be valuable for HPLC-chemiluminescence detection, assuming kinetic behavior in EtOAc/THF is the same as in water/acetonitrile-containing solvents. The data in Table I indicate that the chemiluminescence efficiency of the 2,6-DFPO/CBI-t-BuA system is more than two times greater than that of Dans-ASN/TCPO. Likewise, the chemiluminescence efficiency for 2,6-DFPO/CBI-t-BuA was more than 8 times greater than for 2,6-DFPO/Dans-ASN. All these observations clearly indicate that it is desirable to use 2,6DFPO instead of TCPO for chemiluminescence detection of CBI derivatives in a flow system.

EXAMPLE 1

Chemiluminescence Efficiencies of CBI-t-BuA Adducts using various Oxalate Esters.

The efficiencies of light generation using CBI-t-BuA were compared for various oxalate esters. Again, it was found that 2,6-DFPO gave the greatest total chemiluminescence efficiency not only in comparison with TCPO (see Table I) but also in comparison with 2,4-DNPO and 2,4-DFPO.

A solution of CBI-t-BuA prepared in the same manner as in Comparative Example I above was employed except that the CBI-t-BuA was stored at room temperature for 6 weeks prior to use. Freshly prepared 1 mM solutions of oxalate ester in ethyl acetate were used. The chemiluminescence yield below is in arbitrary units to measured as described in Table I but at an emission of 505 nm (20% less intense than at 480 nm).

TABLE II

| CBI-t-BuA by Various Oxalate Esters | |
|---|---|
| Oxalate Ester | Total chemiluminescence Yield |
| 2,4-DFPO | 5,700 |
| 2,6-DFPO | 16,000 |
| TCPO | 5,300 |
| 2,4-DNPO | 12,700 |

COMPARATIVE EXAMPLE 2

Chemiluminescence Efficiency of CBI-ALA versus Dans-ASN in 2,6DFPO and 2,4-DFPO oxalate esters.

The Dans-ASN solution employed was a stock solution containing $3.8 \times 10^{-6}$M Dans-ASN in a solvent comprising a mixture of 98% water and 2% THF. Three samples of Dans-ASN with 2,6-DFPO oxalate ester were analyzed, the room temperature storage times of which were 4, 12 and 36 hours respectively.

The CBI-ALA employed was a $3.8 \times 10^{-6}$M stock solution in a solvent comprising a mixture of 98% $H_2O$ and 2% THF. This solution was prepared by dissolving the appropriate weight of CBI-ALA in the THF/$H_2O$ solution. Chemiluminescence was measured at 505 nm for Dans-ASN and at 480 nm for CBI-ALA using the static system previously described. The results of the above-described comparison are set forth in Table III below:

TABLE III

| Comparison of the Total Chemiluminescence Efficiencies Generated Using CBI—ALA Versus Dans-ASN, in 50% $H_2O$; 42% THF; 8% EtOAc. Stability of the Derivatized Amino Acids in $H_2O$/THF solution | | | |
|---|---|---|---|
| Oxalate Ester | Dans-ASN | CBI—ALA | Chemiluminescence ratio |
| 2,6-DFPO | 400 (4) | 14,100 (4) | 1:33 |
| | | 12,200 (5) | |
| | 400 (12) | 5,500 (12) | |
| | 400 (36) | 100 (36) | |
| 2,4-DFPO | not measured | 3,900 (6) | |

The difference in the total chemiluminescence efficiency for CBI derivatives and Dans-ASN was even more dramatic for CBI-ALA in water containing solvents (Table III). As the results indicate, the chemiluminescence efficiency for CBI-ALA was about 33 times greater than for Dans-ASN. A similar comparison in an organic solvent system gave only an 8 times enhancement of the chemiluminescence for CBI-t-BuA (Table I). This result confirms the prediction that much better sensitivities for detection might be achieved in an HPLC-chemiluminescence system by using CBI derivatized amines instead of the dansylated analogs when the eluting mixture contains considerable amounts of water, which is often the situation in HPLC fractionations.

The kinetics for chemiluminescence emission in water containing solutions were substantially different from those in organic solvents. Only one maximum was observed in contrast to the two or more seen in organic solvents. A decrease in intensity of 50 to 75% was noted in 4 and 14 s after mixing the chemiluminescence reagents. The overall chemiluminescence efficiency was also much lower in water containing media. However, the decrease in the intensity was much more severe in the case of Dans-ASN (1:52) than for the CBI derivatives (1:13).

The preliminary studies of the stability of CBI and Dansyl derivatives stored in water containing medium at room temperature and exposed to room light for four hours, indicated a decrease in chemiluminescence efficiency of about 13% for CBI-ALA (Table IV, infra). The Dans-ASN chemiluminescence efficiency remained unchanged for up to 36 h. However, the stability of CBI-ALA (Table IV) was found to be much greater than for CNI-ALA, especially when the sample was protected from light and stored in a refrigerator.

EXAMPLE 2

Chemiluminescence Efficiencies Generated Using CBI-ALA versus CNI-ALA

The efficiency of the chemiluminescence emission of CBI-ALA was compared with the analogous CNI-ALA using the oxalate esters 2,6-DFPO and TCPO.

The 2,6-DFPO and TCPO were 0.1M stock solutions in an ethyl acetate solvent and were stored for 8 and 14 days respectively.

The chemiluminescence of CBI-ALA was monitored at 480 nm with a Aminco-Bowman spectrofluorometer detector as described above. The chemiluminescence of CNI-ALA was monitored at 580 nm which corresponds to the maximum wavelength of the CNI-ALA adduct fluorescence. The detector photomultiplier tube sensitivity was approximately 50% at 580 nm compared to the sensitivity at 480 nm. The half-width of the fluorescence peak of CNI-ALA was much larger than for CBI-ALA.

The results of the above-described comparative tests are set forth in Table IV as follows:

TABLE IV

| Comparison of Chemiluminescence Efficiencies of CBI—ALA and CNI—ALA with DFPO and TCPO Oxalate Esters | | |
|---|---|---|
| Oxalate Ester | CBI—ALA | CNI—ALA |
| 2,6-DFPO | 198,000 | 24,700 |
| TCPO | 77,000 | 12,400 |

The CNI derivative gave significantly lower overall chemiluminescence efficiencies than the CBI derivative for both TCPO and 2,6-DFPO. However, these chemiluminescence emissions were monitored at two different wavelengths (480 and 580 nm for CBI and CNI, respectively) and thus are subject to the differences in the photomultiplier tube sensitivity. Taking this difference into account, the chemiluminescence efficiencies for the CNI derivative in Table IV should be doubled. Also, the half-width of the fluorescence emission peak for the CNI derivative is much larger than for the CBI derivative, which leads to lower intensity of chemiluminescence at the maximum wavelength of the emission, where these kinetic measurements were made. However, even after taking into account these highly unfavorable conditions, the total chemiluminescence efficiency for the CNI-ALA derivative in organic solvents seems to be lower than for the corresponding CBI derivative. The plot of chemiluminescence intensity versus time for CNI-ALA showed three maxima, similar to the behavior for the CBI derivatives in organic solvents.

As in the case of CBI derivatives, the results in Table IV, infra, clearly indicate that the chemiluminescence efficiency of CNI-derivative was almost two times higher when 2,6-DFPO was used as the chemiluminescence activator instead of TCPO for chemiluminescence detection of CNI derivatives.

The comparison of the total chemiluminescence efficiency of CBI-t-BuA (Table I) with CBI-ALA (Table IV) under the same reaction conditions with 2,6-DFPO as the chemiluminescence activator indicated that the efficiency does not change appreciably for the derivatized amino acid, CBI-ALA, in comparison with the derivatized amine, CBI-t-BuA. Therefore, the conclusions about the relative chemiluminescence efficiencies for CBI-t-BuA in different oxalate ester systems should be equally valid for other CBI-amino acid derivatives.

EXAMPLE 3

Studies in the Flow High Performance Liquid Chromatography-Chemiluminescence Post Column Detection System Studies were performed which were designed to compare the results obtained in the static system (carried out primarily in the pure organic solvent media), with an HPLC-chemiluminescence flow detector system. A second goal was to find the best conditions for chemiluminescence detection of CBI derivatized amino acids and to compare the limits of detection (LOD) of these derivatives with LOD for dansylated amino acids.

Figure 4:
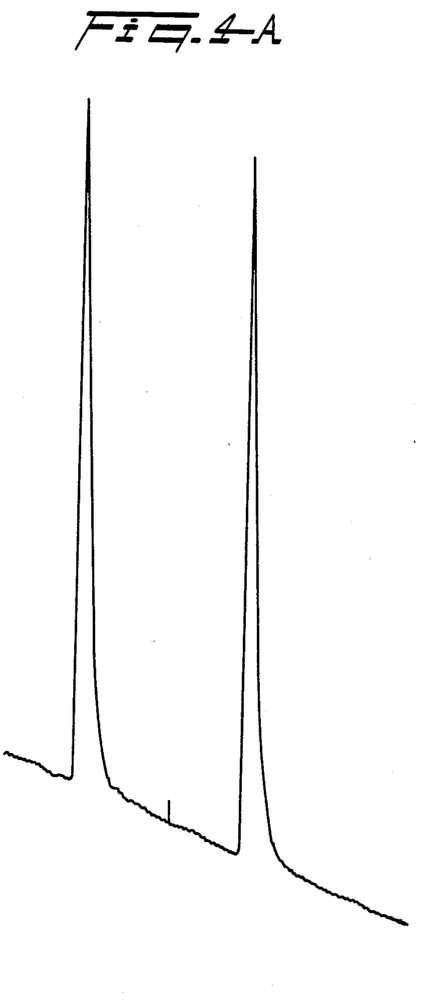

The same detection and HPLC conditions were employed here as described in Comparative Example 1, with one exception; in the HPLC mobile phase, $H_2O$ was replaced by buffer solution consisting of 0.0025M imidazole in $H_2O$ (pH=7.2, adjusted with HCl). Under such conditions, the chemiluminescence signal increased approximately by about a factor of 3 in comparison with the signal presented in FIG. 4. The dipeptide stock solutions were prepared as follows: 0.0446 mg of CBI-ALA-ALA was dissolved in water (stock A); 20 microliter of stock A was diluted with 980 microliters $H_2O$ to give stock B, which contained 2.5 pmol of dipeptide in 5 microliters.

The results of the above-described tests are set forth in Table V as follows:

TABLE V

Comparison of Chemiluminescence Signal Response for Cyanobenz(f)isoindole Derivatives of Alanine (CBI—ALA) and Alanyl—Alanine (CBI—ALA—ALA) in HPLC-Chemiluminescence Flow Detection System.

| CBI Derivative | Amount Injected [pmol] | Peak Height [mm] | Peak Height/ 1 pmol [mm] |
|---|---|---|---|
| ALA | 3.6 | 695 | 199 |
| ALA—ALA | 2.5 | 540 | 216 |

Additionally, in FIG. 4, a comparison of the chemiluminescence versus fluorescence detection of CBI-ALA in a flow HPLC system are set forth. More specifically, the following samples were prepared and analyzed: a stock solution of 7.5 mg of CBI-ALA in 100 mL $H_2O$, stored for 2 months at room temperature, was used (stock A). 20 microliters of stock A was diluted with 380 microliters $H_2O$, to give stock B which contained 71 pmol of CBI-ALA in 5 microliters. Stock C was prepared by diluting 20 microliters of stock B with 380 microliters $H_2O$, to give a solution containing 3.6 pmol of CBI-ALA in 5 microliters. 5 microliter samples were injected into HPLC system. Fluorescence detection conditions were as follows: excitation wavelength= 390 nm, excitation filter (7-59), emission filter wavelength >418 nanometer range =0.1 microamperes photomultiplier tube voltage=510V.

Chemiluminescence detection conditions: syringe pump A: 0.005 M TCPO in EtOAc (448.9 mg of TCPO in 200 mL EtOAc), flow rate 1 mL/min: syringe pump B - 1M $H_2O_2$ in THF (45.2 mL of 30% $H_2O_2$) was diluted to 400 mL with THF, flow rate 2 mL/min; excitation lamp off; emission filter wavelength >418 nm; range=0.02 microamperes; photomultiplier tube voltage=510V. HPLC conditions: mobile phase, 30% MeCN/70% $H_2O$, isocratic, flow rate: 1 mL/min; column: 25 cm×4.6 mm Supelcosil LC-18, volume of stocks B and C injected; 5 microliters.

In FIG. 4 a comparison of the chemiluminescence versus fluorescence detection of CBI-ALA in a flow HPLC system is presented.

The comparison of the sensitivity of chemiluminescence versus fluorescence detection for CBI derivative of ALA, was first carried out using TCPO as the chemiluminescence activator (FIG. 4). The signal obtained from the chemiluminescence detection system was at least 80 times more intense (peak height) than from the direct fluorescence detection when measured at the same signal to noise ratio (S/N) of 3:1. The fluorescence detection conditions were set up to give the optimum sensitivity for detection whereas no such optimization was attempted for chemiluminescence detection. Furthermore, TCPO was used here as the most readily available oxalate ester. Even under these conditions an LOD of 8 femtomole (amount injected) for CBI-ALA was readily achievable (Scheme 2 and Table IV).

The signal intensities obtained with the chemiluminescence detector for CBI derivatives of an amino acid and of a dipeptide were also compared. As the data in Table V indicates, essentially the same signal intensities were obtained for both the amino acid and the dipeptide. This observation might be of great value, since amino acid esters and peptides produce relatively low fluorescence yield derivatives with the ophthaldehyde/thiol reagent system.

COMPARATIVE EXAMPLE 3

Comparison of the Sensitivity of Detection of CBI Derivatives with Dansyl Derivatives by HPLC with Chemiluminescence Detection.

The most important and interesting experiment was the comparison of the sensitivity of detection of CBI derivatives with dansyl derivatives by HPLC with chemiluminescence detection.

Chemiluminescence detection conditions were the same as described in FIG. 4. TCPO was used as the chemiluminescence activator. HPLC analyses were performed as described in FIG. 4. The following samples were prepared and analyzed: Dans-ASN, 0.295 mg/4 mL $H_2O$ (stock A), 20 microliters of stock A was diluted with 380 microliters $H_2O$ (stock B), 20 microliters of stock B was diluted with 380 microliters $H_2O$ (stock C, 5 microliters contained 2.5 pmol); Dans-GLY, 0.165 mg/4 mL $H_2O$ (stock A1), 20 microliters of stock A1 diluted with 380 microliters $H_2O$ (stock B1), 20 microliters of stock B1 was diluted with 380 microliters $H_2O$ (stock C1, 5 microliters contained 1.65 pmol); CBI-ALA, 0.2100 mg/4 mL $H_2O$ (stock A'), 20 microliters of stock A' was diluted with 380 microliters $H_2O$ (stock B'), 20 microliters of stock B' were diluted with 380 microliters H$_2$O (stock C', 5 microliters contained 2.3 pmol), 20 microliters of stock C' was diluted with 380 microliters of H$_2$O (stock D', 5 microliters contained 115 fmoles). Chemiluminescence detection conditions for both dansyl and CBI derivatives were as follows: excitation lamp off, emission filter with an emission wavelength >418 nm, photomultiplier tube voltage=510V, range=0.2 microamperes, time constant=6 s.

For fluorescence detection, mixer M$_2$ (FIG. 3) was removed, and effluent from the HPLC column was delivered directly to the chemiluminescence detector with 10 cm×0.25 mm stainless steel tubing. Fluorescence detection conditions were as follows: for dansyl derivatives, excitation wavelength=340 or 360 nm with excitation filter 7-54 and 7-51, respectively, photomultiplier tube voltage=502V, range=0.1 microampere, time constant=6 s, emission filter wavelength >418 nm; for CBI derivative, excitation wavelength=390 nm, excitation filter 7-59, photomultiplier tube voltage=518V, range=0.1 microampere, time constant=6 s, emission filter wavelength >418 nm.

Ratio of the limits of detection (LOD) for fluorescence detection (LOD$_f$) versus chemiluminescence detection (LOD$_{CL}$), both calculated at the signal to noise (S/N) ratio equal to 3:1.

Limit of detection (LOD) at S/N=3/1.

Since maximum peak heights were taken for calculating LODs, and because the retention time for CBI derivative, under isocratic conditions, was significantly longer than for dansyl derivatives, the observed broadening of the peak makes the value of the LOD for CBI relatively higher than the LOD measured under the same conditions for the dansyl derivatives.

The results of the above-described tests are set forth in Table VI as follows:

Since the TCPO/dansyl derivative system is considered to be the most sensitive method for HPLC/chemiluminescence determination of amino acids presently available (an LOD of 0.5 fmole was reported using single photon counting from a spiral detection cell and a cooled photomultiplier tube), it would appear that the use of the CBI derivatives would lower the detection limit even further, by as much as an order of magnitude.

The data in Table VI also confirm that the LODs achievable by chemiluminescence detection are far superior to the limits obtained with fluorescence detection for either dansyl or CBI amino acid derivatives. Under our analysis conditions, the detection sensitivity of dansylated amino acids has been increased by a factor of 50 to 180 for chemiluminescence versus fluorescence monitoring. A similar factor for CBI derivatives was about 570, indicating a definite advantage with the chemiluminescence method.

EXAMPLE 4

Signal Intensities Obtainable with 2,6-DFPO versus TCPO Oxalate Esters in the HPLC-Chemiluminescence Flow System for both CBI and Dansyl Derivatives.

HPLC conditions were as follows: 15 cm×4.6 mm Supelcosil LC-18 column, mobile phase 25% MeCN/75% 0.0025M imidazole buffer (pH=7.2), flow rate 1 mL/min., isocratic separation, volume injected was 5 microliters. Concentrations of the oxalate esters were the same (0.005M). In the case of 2,6-DFPO, 314.2 mg of oxalate ester were dissolved in 200 mL EtOAc, placed in syringe pump A and pumped to the system with a flow rate of 1 mL/min. Otherwise, the chemiluminescence detection was performed as described in FIG. 4 and Table V, supra.

Stock solutions C and D' described in Example 3 were used for Dans-ASN and CBI-ALA, respectively.

TABLE VI

Comparison of Sensitivity of HPLC - Chemiluminescence Detection for Cyanobenz(f)isoindole Derivative of Alanine (CBI—ALA) With Some Dansyl Derivatized Amino Acids. Sensitivity of Fluorecence Detection of the Same Derivatives.

| Derivative | Chemiluminescence | | | | Fluorescence LOD [pmol] | Ratio |
|---|---|---|---|---|---|---|
| | peak height per 1 pmol [rb. unit] | ret. time [min] | ret. peak height | LOD [fmol] | | |
| Dans-APAR | 25 | 2 | 1.0 | 60 | 11 | 180 |
| Dans-GLY | 10 | 3 | 0.4 | 100–150 | 7 | 50–70 |
| CBI—ALA | 196 | 5 | 7.8 | 8 | 4 | 570 |

The above results clearly indicate that the sensitivity of chemiluminescence detection of the CBI derivatized alanine is about 8 and 20 times greater than for dansyl derivatives of asparagine and glycine, respectively. Such an increase in sensitivity was achieved using TCPO as the chemiluminescence activator. One can conclude that the sensitivity for detection of amines, amino acids and dipeptides can be improved by at least one order of magnitude by employing CBI instead of dansyl derivatization and chemiluminescence detection.

25 cm×4.6 mm Supelcosil LC-18 column was used.

In this experiment the higher absolute signal intensity for 2,6-DFPO might be due to the decrease in the HPLC column length from 25 to 15 cm. In the latter case, retention time was shorter, peaks were sharper, and peak heights were relatively higher. Also, the baseline stability was not as good here as in other experiments. The LOD value reported is at S/N=3/1.

The results of the above-described tests are set forth in Table VII as follows:

TABLE VII

Comparison of HPLC - Chemiluminescence Detection of Dansyl-Asparagine (Dans-ASN) and Cyanobenz(f)isoindole Derivative of Alanine (CBI—ALA), Using TCPO and 2,6-DFPO as the chemiluminescence activators.

| Derivative | Amount Injected | Peak Height [arb. unit] | | Ratio of Signal Int. | LOD[fmol] | |
|---|---|---|---|---|---|---|
| | | TCPO | 2,6-DFPO | 2,6-DFPO/TCPO | TCPO | 2,6-DFPO |
| Dans-ASN | 2.5 pmol | 60 | 112 | 1.9 | 60 | 64 |
| CBI—ALA | 115 fmol | 24 | 55 | 2.3 | 8 | 3 |

The results presented in Table VII indicate that by employing 2,6-DFPO as a chemiluminescence reagent, a sensitivity which is more than two times greater than that obtained with the CBI derivatives could be achieved, which translates into an LOD of from 8 to 3 femtomole. This shows that the CBI derivative-chemiluminescence detection system with 2,6-DFPO is the most sensitive method for the determination of amino acids reported to date. With this system, the sensitivity of detection could be increased by about 20 to 40 times in comparison to the best currently available method, i.e., the dansyl derivatives/TCPO system.

An absolute signal increase was also observed for Dans-ASN when TCPO was replaced by 2,6-DFPO. However, due to the increase in the background noise and HPLC column length, the LOD value at S/N=3/1 remained practically unchanged for both the TCPO and the 2,6-DFPO esters.

Figure 5:
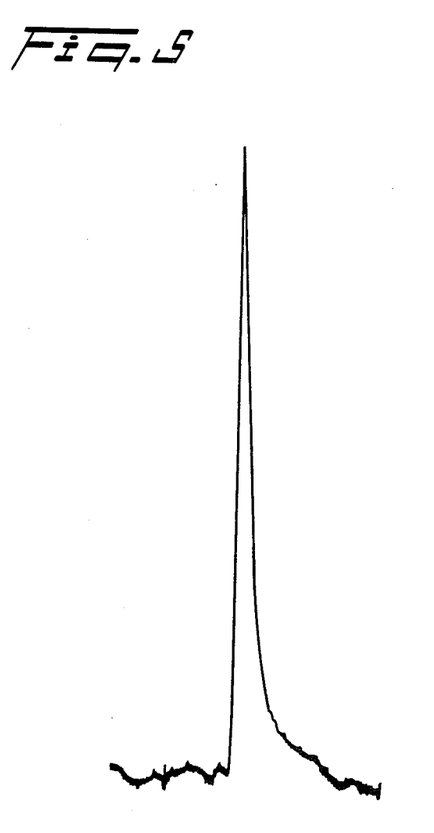
FIG. 5 is a graph depicting the High Performance Liquid Chromatography Chemiluminescence Detection Signal for CBI-ALA.

The detection limits cited in this report were obtained without any effort to optimize the HPLC-chemiluminescence detection system. In FIG. 5 a typical chemiluminescence signal for CBI-ALA is presented.

This signal corresponded to 115 fmole of the injected derivatized analyte with the provision that the CBI-ALA was stable in the stock solution stored for 2 weeks in the refrigerator. It should be noted that the TCPO ester (not 2,6-DFPO ester) was employed as the chemiluminescence activator in this analysis.

The conditions of the test depicted in FIG. 5 were as follows:

HPLC conditions: 15 cm×4.6 mm Supelcosil LC-18 column, mobile phase 30% MeCN/70% 0.0025M imidazole buffer (pH=7.2), isocratic elution with a flow rate of 1 mL/min, retention time was 1 min and 40 s.

Chemiluminescence detection conditions were the same as described in FIG. 4, but photomultiplier voltage was 600V, time constant 10 s, range=0.01 microamperes, TCPO was used as the chemiluminescence activator.

5 microliters of freshly prepared stock D' (see Example 3) was injected and analyzed. This corresponds to 115 fmol of CBI-ALA injected. Stock D' was prepared from stock A', the latter being stored for two weeks in the refrigerator.

From the foregoing Examples and Comparative Examples, it is evident that CBI derivatives of selected amines, amino acids and small peptides are excellent energy acceptors (fluorescers) in the oxalate - $H_2O_2$ chemiluminescence detection system.

The results obtained in the investigation of the static system indicate that CBI derivatives of amines and amino acids are capable of generating higher total chemiluminescence efficiencies than the dansylated derivatives of amino acids. This effect was especially pronounced in aqueous solutions, which are typically employed in HPLC techniques. In fact, the fluorescence quantum efficiency of the inventive CBI adducts remains nearly unchanged when aqueous rather than organic solvents are employed. In contrast to the CBI adducts, the quantum efficiency of fluorescence of dansylated analogs was observed to decrease considerably, i.e., from 0.3 to 0.7 in organic solvents to 0.053 to 0.091 in aqueous solvents. This represents a significant development in the art since HPLC/chemiluminescence detection of dansylated amino acids with TCPO/$H_2O_2$, using state-of-the-art electronic equipment for light collection and photon counting, had been considered to be the most sensitive detection method for amino acids. The utilization of CBI derivatives and 2,6-DFPO, however, should lower the detection limit of primary amine analytes by at least a factor of 20 to 40 relative to the dansyl-TCPO system previously employed and by as much as an order of magnitude. This translates to a detection limit below the 0.1 femtomole level.

Since the detection limits observed for CBI-dipeptide analytes (ALA-ALA) were comparable to those obtained with CBI-ALA using the inventive assaying method, it is clear that the present invention is applicable generally to sensitive detection of small peptides.

Although only preferred embodiments are specifically illustrated and described herein, it will be appreciated that many modifications and variations of the present invention are possible in light of the above teachings and within the purview of the appended claims without departing from the spirit and intended scope of the invention.

What is claimed is:

1. A method for assaying compounds containing a primary amino group comprising the steps of:
   (i) contacting a sample which includes a compound containing a primary amino group with (A) naphthalene-2,3-dicarboxaldehyde or anthracene-2,3-dicarboxaldehyde and (B) cyanide such that the compound containin a primary amino group reacts with (A) and (B) to form a 1-cyano-2-substituted benz(f)isoindole fluorescer when (A) is naphthalene-2,3-dicarboxaldehyde or a 1-cyano-2-substituted-naphth(f)isoindole fluorescer when (A) is anthracene-2,3-dicarboxaldehyde;
   (ii) mixing an oxalate ester and hydrogen peroxide with the fluorescer formed in step (i) to form an analyte exhibiting chemiluminescence; and
   (iii) detecting and measuring chemiluminescent emission from said analyte by means of a detector.

2. The method of claim 1 wherein (A) is naphthalene-2,2-dicarboxaldehyde.

3. The method of claim 1 wherein the sample is a solution which includes the compound containing a primary amino group at a concentration of about 1 nanomolar.

4. The method of claim 1 wherein said compound containing a primary amino group is alanine or tert-butyl amine.

5. The method of claim 1 wherein said compound containing a primary amino group is a catecholamine.

6. The method of claim 1 wherein the compound containing a primary amino group is a primary amine, a primary amino acid, a peptide bearing at least one primary amino group, or a catecholamine.

7. The method of claim 6 wherein the compound containing a primary amino group is the peptide Alanyl-Alanine.

8. The method of claim 1 wherein said oxalate ester is bis-(2,6-difluorophenyl) oxalate, bis-(2,4-difluorophenyl) oxalate, bis-(2,4,6-trichlorophenyl) oxalate, bis-(2,4-dinitrophenyl) oxalate or bis-(pentafluorophenyl) oxalate.

9. The method of claim 8 wherein said oxalate ester is bis-2,6-difluorophenyl) oxalate or bis-(2,4-difluorophenyl) oxalate.

10. The method of claim 8 wherein said oxalate ester is bis-(2,6-difluorophenyl) oxalate.

11. The method of claim 1 wherein the sample includes a plurality of compounds containing a primary amino group and wherein the method further comprises the step of fractionating the sample prior to or after step (i).

12. The method of claim 11 wherein said fractionating step is carried out by high performance liquid chromatography.

13. The method of claim 11 wherein said fractionating step is carried out after said step (i).

14. The method of claim 13 wherein said fractionating step is carried out by high performance liquid chromatography.

15. The method of claim 14 wherein said fractionation by high performance liquid chromatography is carried out in an aqueous medium.

16. A method for assaying trace quantities of cyanide in a sample comprising the steps of:
(i) contacting a sample which includes cyanide with known quantities of (A) naphthalene-2,3-dicarboxaldehyde or anthracene-2,3-dicarboxaldehyde and (B) a compound containing a primary amino group such that the cyanide reacts with (A) and (B) to form a 1-cyano-2-substituted benz(f)isoindole fluorescer when (A) is naphthalene-2,3-dicarboxaldehyde or a 1-cyano-2-substituted-naphth(f)isoindole fluorescer when (A) is anthracene-2,3-dicarboxaldehyde;
(ii) mixing an oxalate ester and hydrogen peroxide with the fluorescer formed in step (i) to form an analyte exhibiting chemiluminescence; and
(iii) detecting and measuring chemiluminescent emission from said analyte by means of a detector.

17. A method for assaying trace quantities of hydrogen peroxide in a sample comprising the steps of:
(i) mixing a sample containing hydrogen peroxide with an oxalate ester;
(ii) adding a known quantity of a pre-made 1-cyano-2-substituted benz(f)isoindole fluorescer or a 1-cyano-2-substituted-naphth(f)isoindole fluorescer to the sample to form an analyte exhibiting chemiluminescence; and
(iii) detecting and measuring chemiluminescent emission from said analyte by means of a detector.

* * * * *